United States Patent
Sayles et al.

(10) Patent No.: US 10,470,809 B1
(45) Date of Patent: Nov. 12, 2019

(54) AUTOMATED SCREW IDENTIFICATION SYSTEM AND METHOD

(71) Applicant: Summate Technologies, Inc., Newburyport, MA (US)

(72) Inventors: Philip Sayles, Newburyport, MA (US); Todd Rosseau, Newburyport, MA (US)

(73) Assignee: Summate Technologies, Inc., Newburyport, MA (US)

( * ) Notice: Subject to any disclaimer, the term of this patent is extended or adjusted under 35 U.S.C. 154(b) by 0 days.

(21) Appl. No.: 16/012,652

(22) Filed: Jun. 19, 2018

(51) Int. Cl.
| | |
|---|---|
| *G06F 19/00* | (2018.01) |
| *A61B 17/86* | (2006.01) |
| *A61B 50/33* | (2016.01) |
| *A61B 90/98* | (2016.01) |
| *G06K 19/00* | (2006.01) |
| *G06K 7/10* | (2006.01) |
| *A61B 90/00* | (2016.01) |
| *A61B 50/30* | (2016.01) |

(52) U.S. Cl.
CPC ........... *A61B 17/865* (2013.01); *A61B 50/33* (2016.02); *A61B 90/98* (2016.02); *G06K 19/005* (2013.01); *A61B 90/06* (2016.02); *A61B 2050/3008* (2016.02); *A61B 2090/061* (2016.02); *G06K 7/10386* (2013.01); *G06K 7/10881* (2013.01); *G06K 2007/10504* (2013.01)

(58) Field of Classification Search
CPC ......... A61B 50/20; A61B 50/30; A61B 50/33; G06Q 10/087; G06Q 10/08; G06Q 10/0875; G06Q 50/22
USPC ...................................................... 235/385
See application file for complete search history.

(56) References Cited

U.S. PATENT DOCUMENTS

| | | | |
|---|---|---|---|
| 3,967,202 A | 6/1976 | Batz | |
| 4,614,945 A | 9/1986 | Brunius | |
| 4,816,839 A | 3/1989 | Landt | |
| 5,234,433 A * | 8/1993 | Bert .................. | A61B 17/154 606/102 |
| 5,528,222 A | 6/1996 | Moskowitz | |
| 5,641,634 A | 6/1997 | Mandecki | |
| 5,682,143 A | 10/1997 | Brady | |

(Continued)

FOREIGN PATENT DOCUMENTS

| | | |
|---|---|---|
| KR | 100875690 | 8/2007 |
| KR | 20070078826 | 8/2007 |

(Continued)

OTHER PUBLICATIONS

Telemetry Group "Telemetry Standard RCC Document 106-07," Chapter 2, Sep. 2007.

(Continued)

*Primary Examiner* — Thien M Le
(74) *Attorney, Agent, or Firm* — Blueshift IP, LLC; Robert Plotkin (57) ABSTRACT

A tray includes a plurality of rows, each of which includes a plurality of slots. Each row contains a plurality of screws. Different rows may contain screws of different types, e.g., lengths. Each of one or more rows contains a machine-readable object (e.g., peg) containing data representing properties of the objects in the corresponding rows. Removal of an object from a row is performed by reading data from the machine-readable object in the row and using that data to modify (e.g., decrement or increment) a count of the type of object contained in that row.

8 Claims, 4 Drawing Sheets

(56) References Cited

U.S. PATENT DOCUMENTS

| | | |
|---|---|---|
| 5,786,626 A | 7/1998 | Brady |
| 5,825,298 A | 10/1998 | Walter |
| 5,874,902 A | 2/1999 | Heinrich |
| 5,892,458 A | 4/1999 | Anderer |
| 5,974,078 A | 10/1999 | Tuttle |
| 6,104,281 A | 8/2000 | Heinrich |
| 6,147,662 A | 11/2000 | Grabau |
| 6,177,859 B1 | 1/2001 | Tuttle |
| 6,293,684 B1 | 9/2001 | Riblett |
| 6,590,150 B1 | 7/2003 | Kiefer |
| 6,925,447 B2 | 8/2005 | McMenimen |
| 7,053,294 B2 | 5/2006 | Tuttle |
| 7,098,394 B2 | 8/2006 | Armer |
| 7,135,977 B2 | 11/2006 | Burg |
| 7,195,149 B2 | 3/2007 | Baker |
| 7,328,837 B2 | 2/2008 | Baker |
| 7,412,898 B1 | 8/2008 | Smith |
| 7,585,302 B2 | 9/2009 | Revie |
| 7,633,111 B2 | 12/2009 | Friedrich |
| 7,698,156 B2 | 4/2010 | Martucci |
| 7,791,481 B2 | 9/2010 | Landt |
| 7,849,807 B2 | 12/2010 | Suzuki |
| 7,915,517 B2 | 3/2011 | Lau |
| 8,027,632 B2 | 9/2011 | Mazar |
| 8,089,285 B2 | 1/2012 | Hsu |
| 8,165,658 B2 | 4/2012 | Waynik |
| 8,350,704 B2 | 1/2013 | Mullis |
| 8,353,917 B2 | 1/2013 | Mandecki |
| 8,476,689 B2 | 7/2013 | Chang |
| 8,540,468 B2 | 9/2013 | Mekid |
| 8,552,470 B2 | 10/2013 | Chen |
| 8,574,946 B1 | 11/2013 | Martin |
| 8,576,050 B2 | 11/2013 | Hansen |
| 8,587,406 B2 | 11/2013 | Maltseff |
| 8,587,410 B2 | 11/2013 | Potyrailo |
| 8,596,544 B2 | 12/2013 | Kang |
| 8,616,459 B2 | 12/2013 | Sykkoe |
| 8,624,294 B2 | 1/2014 | Kline |
| 8,628,018 B2 | 1/2014 | Zenz |
| 8,636,220 B2 | 1/2014 | Warther |
| 8,660,640 B2 | 2/2014 | Markowitz |
| 8,663,120 B2 | 3/2014 | Markowitz |
| 8,717,430 B2 | 5/2014 | Simon |
| 8,996,393 B2 | 3/2015 | Sobie |
| 9,313,558 B1 | 4/2016 | Mandecki |
| 9,361,568 B2 | 6/2016 | Butler |
| 9,370,401 B2 | 6/2016 | Sayles |
| 9,405,950 B2 | 8/2016 | Mats |
| 9,418,263 B2 | 8/2016 | Butler |
| 9,418,321 B1 | 8/2016 | Gruda |
| 9,847,044 B1* | 12/2017 | Foster ............... G09B 23/28 |
| 9,964,134 B1 | 5/2018 | Tran |
| 2003/0146836 A1 | 8/2003 | Wood |
| 2004/0019464 A1 | 1/2004 | Martucci |
| 2004/0078231 A1 | 4/2004 | Wilkes |
| 2004/0172302 A1 | 9/2004 | Martucci |
| 2005/0102167 A1 | 5/2005 | Kapoor |
| 2005/0125068 A1* | 6/2005 | Hozack ............... A61F 2/389 623/20.32 |
| 2006/0084934 A1 | 4/2006 | Frank |
| 2007/0006887 A1 | 1/2007 | Frank |
| 2007/0135965 A1 | 6/2007 | Nguyen |
| 2007/0290030 A1 | 12/2007 | Fox |
| 2008/0030345 A1* | 2/2008 | Austin ............... A61B 90/90 340/572.8 |
| 2012/0234922 A1 | 9/2012 | Sample |
| 2012/0241524 A1 | 9/2012 | Blot |
| 2012/0318863 A1 | 12/2012 | Kim |
| 2012/0325905 A1 | 12/2012 | Kim |
| 2014/0048900 A1 | 2/2014 | Keysar |
| 2014/0125482 A1* | 5/2014 | Rigsby ............... A61B 17/7001 340/539.13 |
| 2016/0212577 A1 | 7/2016 | Dor |
| 2017/0098049 A1* | 4/2017 | Sweeney ............ G06Q 10/0875 |
| 2018/0322445 A1* | 11/2018 | Sayles ............... G06Q 10/087 |

FOREIGN PATENT DOCUMENTS

| | | |
|---|---|---|
| KR | 100881986 | 2/2009 |
| KR | 101019674 | 10/2010 |
| KR | 20110096700 | 8/2011 |
| KR | 200462233 Y1 | 9/2012 |
| KR | 101197088 B1 | 11/2012 |
| KR | 200475044 Y1 | 10/2014 |
| KR | 101637919 | 7/2016 |
| KR | 101677943 | 11/2016 |
| WO | 2016208784 | 12/2016 |

OTHER PUBLICATIONS

Axisa, F., et al., "Design and fabrication of a low cost implantable bladder pressure monitor," 2009 Annual International Conference of the IEEE Engineering in Medicine and Biology Society, pp. 4864-4867 (2009).

Bazaka, K., and Jacob MV., "Implantable devices: issues and challenges," Electron, vol. 2, pp. 1-34 (2013).

Beck, H., et al., "50th Anniversary of the first successful permanent pacemaker implantation in the United States: historical review and future directions," Am J Cardiel, vol. 106, No. 6, pp. 810-818 (2010).

Fiandra, O., "The first pacemaker implant in America," Pacing Clin Electrophysiol, vol. 11, Issue 8, pp. 1234-1238 (1988).

Food and Drug Administration, Nov. 4, 2014, Retrieved from the Internet: URL: https://www.fda.gov/medicaldevices/.

Furman, S., "Early history of cardiac pacing and defibrillation," Indian Pacing Electrophysiology, vol. 2, No. 1, pp. 2-3 (2002).

Greatbatch, W., and Holmes, CF., "History of implantable devices," IEEE Eng Med Biol Mag, vol. 10, No. 3, pp. 38-41 (1991).

Gruda, MC., et al., "A System for Implanting Laboratory Mice with Light Activated Microtransponders," J. Am. Ass. Lab. Animal Sci., vol. 49, No. 6, pp. 826-831 (Nov. 2010).

Jiang, G. and Zhou, D.D., "Technology Advances and Challenges in Hermetic Packaging for Implantable Medical Devices," Zhou, DD and Greenbaum, ES, Implantable neural prostheses 2, Techniques and Engineering Approaches, pp. 28-61 (2010).

Johnson, J.A., "FDA regulation of medical devices," Congressional research service, Federation of American Scientists, pp. 1-33 (Jun. 25, 2012).

Kileny, PR, et al., "Effects of preoperative electrical stimulability and historical factors on performance with multichannel cochlear implant," Ann Otol Rhinol Laryngol, vol. 100, No. 7, pp. 563-568 (1991).

Larsson, B., et al., "Lessons from the first patient with an implanted pacemaker: 1958-2001," Pacing Clin Electrophysiol, vol. 26, Issue 1 Pt1, pp. 114-124 (2003).

Magjarevic, R., and Ferek-Petric, B., "Implantable cardiac pacemakers: 50 years from the first implantation," Zdravniški vestnik, vol. 79, No. 1, pp. 55-67 (2010).

Majerus, SJ, et al., "Low-power wireless micromanometer system for acute and chronic bladder-pressure monitoring," IEEE Transactions on Biomedical Engineering, vol. 58, Issue 3, pp. 763-767 (2011).

Mokwa, W., "Medical implants based on Microsystems," Measurement Science and Technology, vol. 18, pp. R47-R57 (2007).

Niarasimhan, S., et al., "Implantable electronics: emerging design issues and an ultra light-weight security solution," Conf Proc IEEE Eng Med Biol Soc, pp. 6425-6428 (2010).

Olivo, J., et al., "Energy harvesting and remote powering for implantable biosensors," IEEE Sensors Journal, vol. 11, Issue 7, pp. 1573-1586 (2011).

Onuki, Y, et al., "A review of the biocompatibility of implantable devices: current challenges to overcome foreign body response," J Diabetes Sci Technol, vol. 2, No. 6, pp. 1003-1015 (2008).

Rajappan, K., "Permanent pacemaker implantation technique: Part II," Heart, vol. 95, No. 4, pp. 334-342 (2009).

Robinson, E.J.H., and Mandecki, M., "Distributed Decisions: New Insights From Radio-Tagged Ants," In: Ant Colonies: Behavior in Insects, Nova Science Publishers, Inc. (2010).

(56) References Cited

OTHER PUBLICATIONS

Shlegr, Z, and Egorov, A., "Implantable electric bladder stimulator used for neurogenic failures," Biomed Eng (NY), vol. 7, pp. 382-383 (1974).
Wilson BS, and Dorman MF., "Cochlear implants: a remarkable past and a brilliant future," Hear Res., vol. 242, pp. 3-21 (2008).
Wong, J. Y., et al., "Biomaterials: Principles and Practices," Boca Raton, FL: CRC Press., pp. 281 (2012).
Zoll, PM, "Resuscitation of the heart in ventricular standstill by external electric stimulation," N Engl J Med, vol. 247, No. 20, pp. 768-771 (1952).

\* cited by examiner

AUTOMATED SCREW IDENTIFICATION SYSTEM AND METHOD

BACKGROUND

Modern surgical procedures involve the use of a wide variety of supplies and implants, such as screws, plates, Kirschner wires (K-wires), anchors, and drill bits. It is critical to track and create a record of the type and quantity of the supplies used both inside and outside of the field during a particular surgical procedure for a variety of reasons, such as billing, quality assurance, accurate patient records, and determining the type and quantity of supplies that need to be reordered and restocked. Creating such an accurate record while a surgery is being performed is complicated by a variety of factors, including the wide variety of supplies that are used, difficulty of tracking what is used inside the sterile field, the lack of space on the tray to print the corresponding part number of each distinct screw type, the small size of such supplies, and the difficulty of distinguishing similar supplies from each other, all in real-time while the surgery is being performed. Traditional manual methods for tracking such supply usage, such as visually identifying the supplies that are used and writing down the type and quantity of such supplies on paper or manually recording such supplies in a database, tend to be slow, tedious, and error-prone. Errors in the record of the type and quantity of supplies and implants used can have a variety of negative consequences, including failure of the hospital to be reimbursed for all of the supplies that were used, failure to reorder the correct supplies, lag time in ordering restock supplies in a timely fashion, and errors in the patient's surgical history which can contribute to sub-optimal care for the patient in the future.

What is needed, therefore, are improved techniques for tracking the type and quantity of supplies used during surgery.

SUMMARY

An implant tray includes a plurality of rows, each of which includes a plurality of slots. Each row contains a plurality of screws. Different rows may contain screws of different types, e.g., lengths. Each of one or more rows contains a machine-readable object (e.g., peg) containing data representing properties of the objects in the corresponding rows. Removal of an object from a row is performed by reading data from the machine-readable object in the row and using that data to modify (e.g., decrement or increment) a count of the type of object contained in that row.

Other features and advantages of various aspects and embodiments of the present invention will become apparent from the following description and from the claims.

DETAILED DESCRIPTION

Figure 1:
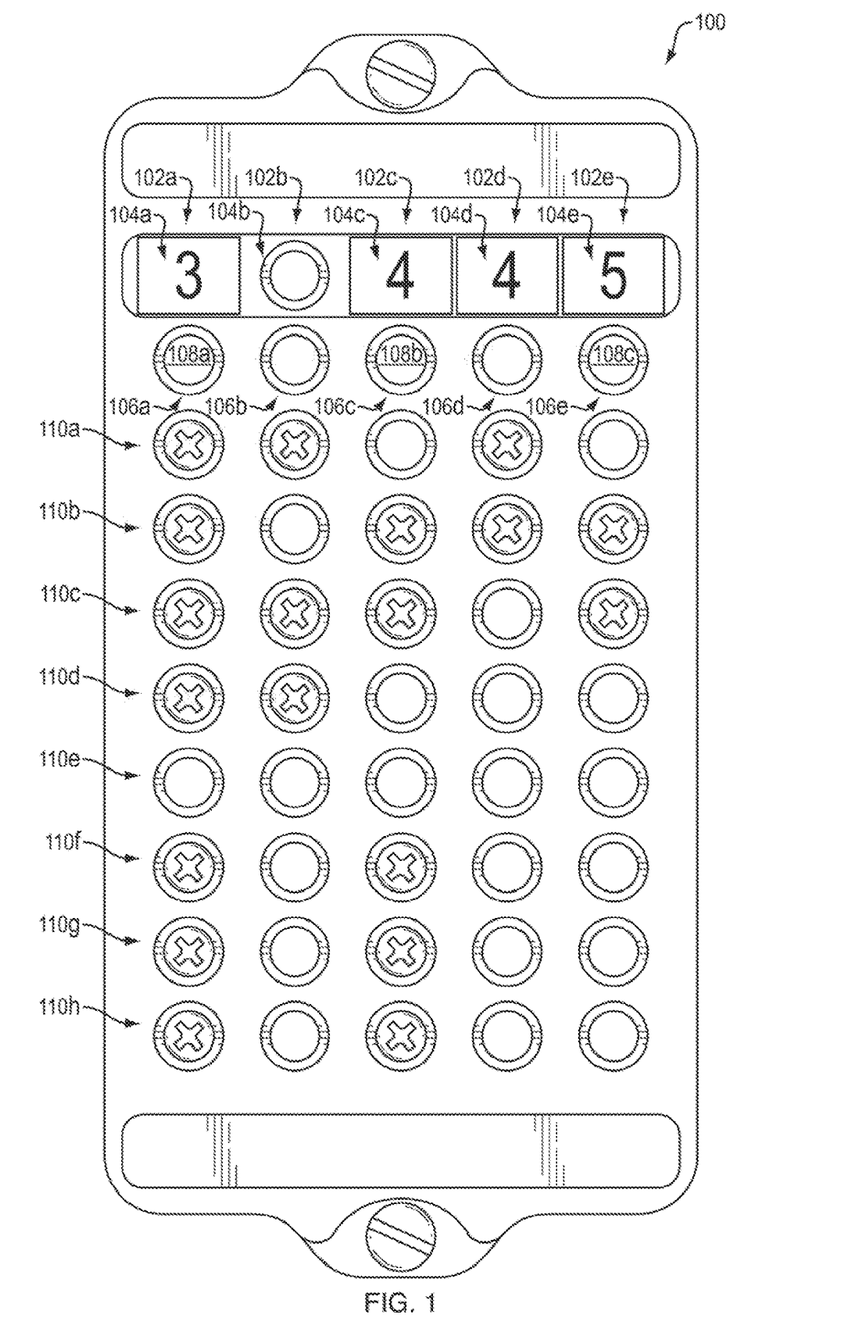
FIG. 1 is an illustration of a surgical plating tray according to one embodiment of the present invention.

Referring to FIG. 1, a surgical plating tray 100 (also referred to in the art as a "set") is shown according to one embodiment of the present invention. For ease of illustration, the tray 100 shown in FIG. 1 is designed solely to hold surgical screws. In practice, the tray 100 may hold other kinds of surgical supplies, such as any of the other kinds of surgical supplies described herein. As another example, in practice the tray 100 may be part of a larger tray which contains other components for holding other kinds of surgical supplies.

As shown in FIG. 1, the surgical plating tray 100 includes a plurality of rows 102a-e. In the particular example of FIG. 1, the tray 100 includes exactly five rows. This is merely an example, however, and does not constitute a limitation of the present invention. More generally, trays implemented according to embodiments of the present invention may include any number of rows. A tray may have an entire module dedicated solely to holding screws, and another module dedicated solely to holding another type of supply, such as plates. As another example, a tray may include a module which holds multiple types of supplies, e.g., both screws and plates. These and other types of trays all fall within the scope of embodiments of the present invention. Similarly, the precise spacing, orientation, and arrangement of the rows shown in FIG. 1 is merely illustrative and not limiting of the present invention.

Furthermore, the tray 100 illustrated in FIG. 1 includes a plurality of slots 104a-e at the tops of corresponding rows 102a-e, respectively. In the particular example shown in FIG. 1, slots 104a, 104c, 104d, and 104e contain screw length markers on which numbers are printed. Such numbers indicate the length of screw contained in the corresponding row. For example, the number 3 on the screw length marker in slot 104a indicates that screws of 3 mm in length are contained in corresponding row 102a. Similarly, the number 4 on the screw length marker in slot 104c indicates that screws of 4 mm length are contained in corresponding row 102c; the number 4 on the screw length marker in slot 104d indicates that screws of 4 mm in length are contained in corresponding row 102d; and the number 5 on the screw length marker in slot 104e indicates that screws of 5 mm in length are contained in corresponding row 102e. As these examples illustrate, the number printed on a particular screw length marker in a particular row indicates the length of the screws that are contained in that particular row.

In the example of FIG. 1, the absence of a screw length marker in a slot indicates that the corresponding row does not contain any screws. For example, the absence of a screw length marker in slot 104b indicates that corresponding row 102b does not contain any screws.

Everything described above in connection with the slots 104a-e and the screw length markers contained in the slots 104a-e is merely an example and does not constitute a limitation of the present invention. For example, some or all of the slots 104a-e may be omitted from the tray 100. Similarly, some or all of the screw length markers may be omitted from the tray 100. Some or all of the screw length markers may contain indicia other than numbers, such as letters, words, bar codes, QR codes, color codes, or any other indicia. Some or all of the screw length markers may be located at positions other than the tops of their corresponding rows, such as in the middle or the bottom of their corresponding row. The screw length markers shown in the slots 104a-e of FIG. 1 may be made of any material(s) and be of any shape(s) and/or size(s). The length of screws in the tray may alternatively be indicated by direct part marking on the actual tray 100 itself, rather than by using screw length markers inserted into the tray.

Each of the rows 102a-e may include a plurality of corresponding slots, which are adapted to receive and hold screws (e.g., surgical screws) and other objects (such as the screw length markers shown in FIG. 1). The slots within a particular row may be arranged in a linear or substantially linear arrangement. Each of the rows 102a-e includes a "topmost" slot at one end of the row and a "bottommost" slot at the other end of the row, although the designation of one end of the row as "topmost" and the other end of the row as "bottommost" is arbitrary and used herein only for ease of reference. More generally, the "topmost" slot refers to the slot at one end of a row and the "bottommost" slot refers to the slot at the other end of the row. For example, in the embodiment illustrated in FIG. 1, slots 104a-e will be referred to herein as the "topmost" slots of their corresponding rows 102a-e for ease of explanation, although those slots may just as easily be defined as the "bottommost" slots of their corresponding rows 102a-e.

The slots in the tray 100 may be adapted to receive and hold screws and/or other objects in any of a variety of ways. For example, in the embodiment illustrated in FIG. 1, each of the slots includes a lower lip, below the exterior surface of the slot, having a surface with an opening having a smaller diameter than the cross-section of the exterior surface of the slot, thereby forming an interior surface on which the head of a screw, peg, or other object may rest when inserted into the slot. For example, referring to FIG. 2, a peg 200 is shown. The peg (also referred to herein as a "pin") includes a relatively short cylindrical head 202 coupled to a relatively long cylindrical shaft 204. In the particular embodiment shown in FIG. 2, the lower portion of the head 202 is beveled at its point of connection to the shaft. The particular shapes and sizes of the head 202 and shaft 204 shown in FIG. 2, including the bevel, are merely examples and do not constitute limitations of the present invention.

Figure 2:
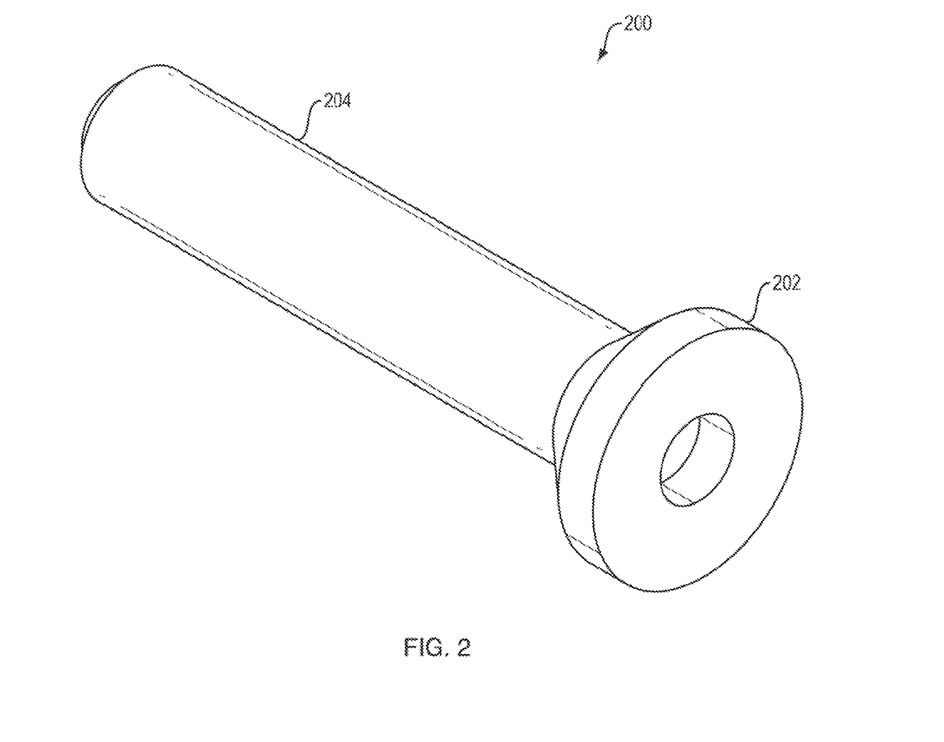
FIG. 2 is an illustration of a peg according to one embodiment of the present invention.

The peg 200 may, for example, be implemented as disclosed in U.S. Pat. No. 9,313,558, entitled, "Tagging of Metal Pins for Mounted Objects with Light-Activated Microtransponders," issued on Apr. 12, 2016, and incorporated by reference herein in its entirety. As disclosed therein, a pin may have a transponder affixed thereto. The transponder may be a very small, light-triggered transponder (referred to as an "MTP" or "p-Chip"). MTPs are generally sided, in that the photocell/RF circuitry is formed on one face, and the other major face is generally silicon—and can be a product of height reduction by back grinding. The circuitry face is generally protected by a passivation layer, such as of silicon dioxide, silicon nitride or mixtures, or multiple such layers.

The peg 200 is an elongated object, and may be made, for example, of metal, plastic, or wood, one end of which has a bulky, often oval shape, called the head of the pin 200, the other end of which may be sharpened. The diameter of the bulky end is typically larger than the diameter of the elongated portion of the peg 200. The axis of the peg 200 goes through the center points of the cross-sections of the elongated portion of the peg 200.

When an object, such as the peg 200, is inserted into one of the slots in the tray 100, such as any one of slots 104a-e or 106a-e, the shaft 204 of the peg 200 may extend into the cylindrical cavity of the slot, below the exterior surface of the slot, and further below the interior surface described above with the narrower cavity. As the peg 200 is further inserted into the slot, the head 202 of the peg 200 will eventually make contact with the protruding interior surface of the slot, thereby preventing the peg 200 from being inserted further into the slot. The result, as illustrated by various pins and screws in the tray 100 of FIG. 1, is that the peg 200 is held in place within its slot, with the upper surface of the peg 200 being level with, or slightly above or below the upper surface of the slot.

In the embodiment illustrated in FIG. 1, the screw length markers in slots 104a, 104c, 104d, and 104e may include shafts (not shown), coupled to the undersides of the numbered surfaces of the screw length markers, which may be the same as or similar to the pin shaft 204 shown in FIG. 2. As a result, the screw length markers may be inserted into and held in place by the slots of the tray 100 in the same or similar manner as the peg 200 of FIG. 2.

In the example described above and illustrated in FIGS. 1 and 2, the slots in the tray 100 are adapted to hold pins and other objects in place using a combination of the interior lip and gravity. This is merely an example and does not constitute a limitation of the present invention. In other embodiments, one or more slots may be adapted to hold pins and other objects in place using other means, such as suction, friction, and/or adhesion.

In the particular example shown in FIG. 1, the slots have a circular cross-section, although this is not a limitation of the present invention. The slots may, for example, have square, hexagonal, octagonal, or other cross-sections.

In the embodiment shown in FIG. 1, within each of the rows 102a-e, the slots that are below the screw length marker in that row are typically used to hold screws. For example, in row 102a, slots 106a and 110a-h typically are used to hold screws of the type indicated by the number or other indicia on the screw length marker in the topmost slot 104a of that row 102a. In embodiments of the present invention, one or more of the slots in a row may be used to contain a machine-readable object, such as a machine-readable pin, which contains data representing information about one or more of the screws (or other supplies) in that row, such as the type of such screws.

For example, in FIG. 1, slot 106a includes a machine-readable object 108a, such as a machine-readable pin, which may be designed in accordance with FIG. 2 and the above-referenced U.S. Pat. No. 9,313,558. Similarly, in the example of FIG. 1, slots 106c and 106e also include such machine-readable objects (e.g., pins).

In the particular example of FIG. 1, machine-readable objects are contained within one or more of the slots 106a-e which are immediately below the topmost slots of rows 102a-e. For example, machine-readable object 108a is contained within slot 106a, which is immediately below topmost slot 104a. Such slots, which are immediately below the topmost slots of each row, are referred to herein as "next topmost slots." This, however, is merely an example and does not constitute a limitation of the present invention. Machine-readable objects may be contained within any slot(s) in any row, such as the topmost slot, the middle slot, the bottommost slot, or any combination thereof. As merely one example, machine-readable objects may be contained within the topmost slots of one or more of the rows 102a-e. For example, the screw length markers shown in FIG. 1 may be machine-readable, using the mechanisms disclosed in U.S. Pat. No. 9,313,558 and/or other mechanisms, thereby eliminating the need to include both the screw length markers and additional machine-readable objects in the tray 100. Instead, in such embodiments, the screw length markers may perform the dual function of providing human-readable indicia of the screws contained within the rows 102*a-e* and providing machine-readable data representing information about the screws contained within the rows 102*a-e*.

Machine-readable objects implemented according to embodiments of the present invention may be clearly visually discernible from the screws or other objects in the same row. For example, in the embodiment illustrated in FIG. 1, the machine-readable pins 108*a-c* have heads with an upper surface that is flat and shiny, making them easy to locate visually. Furthermore, the screws in the tray 100 have Phillips-style heads, which are not flat and which therefore stand out visually from the flat heads of the machine-readable pins 108*a-c*. More generally, pins implemented according to embodiments of the present invention may have one or more visual characteristics which are distinct from one or more visual characteristics of the corresponding screws (or other supplies), thereby causing them to be easily discernible visually from the corresponding screws.

In general, a machine-readable object contained within any one of the rows 102*a-e* may contain a non-transitory storage medium which contains data representing information about one or more properties of one or more of the objects (e.g., screws) that are contained within that row. Examples of such storage media include, for example, radio frequency identification (RFID) tags, light-triggered transponders, integrated circuits (chips), bar codes, and QR codes. The non-transitory storage medium contained in a machine-readable object may use any mechanism to store data. The data contained within a non-transitory storage medium may represent any of a variety of information about the objects contained within the same row as the non-transitory storage medium, such as their manufacturer, model number, part number, stock keeping unit (SKU), length, width, or any combination thereof.

As described above, the data contained within a non-transitory storage medium may be machine-readable. Such data may or may not be human-readable. For example, a non-transitory storage medium may be or include an RFID tag, in which case the data on such a tag may be readable by a machine and not be a human. In some embodiments, however, a non-transitory storage medium and/or a supply (e.g., screw) may include human-readable indicia representing some or all of the same information as represented by the machine-readable data stored on the non-transitory medium. Examples of such indicia include printed symbols (e.g., numbers and/or letters) representing a manufacturer, model number, part number, stock keeping unit (SKU), length, width, or any combination thereof of the supply (e.g., screw). The inclusion of such human-readable indicia may eliminate the need for the human-readable screw length markers described above and shown in FIG. 1. Furthermore, note that some indicia, such as numbers and bar codes, may be both machine-readable and human-readable. Furthermore, the screw length markers may include, instead of or in addition to human-readable indicia representing screw lengths, human-readable indicia representing any one or more of the other properties listed above.

A non-transitory storage medium may be contained within or otherwise coupled to or associated with a machine-readable object in any of a variety of ways. For example, a non-transitory storage medium may be affixed to the head 202 of the peg 200 shown in FIG. 2, such as by using tape or other adhesive means to affix the non-transitory storage medium to the upper surface of the head 202 of the peg 200.

In the particular example shown in FIG. 1, row 102*a* contains: (1) machine-readable object 108*a* (e.g., pin) in slot 106*a*; and (2) screws in slots 110*a-d* and 110*f-h*. Machine-readable object 108*a* includes a non-transitory storage medium containing data representing information about the screws (if any) contains in the slots 110*a-h* of row 102*a*.

In addition, note that the next topmost slot 106*b* of the row 102*b* that is adjacent and immediately to the right of row 102*a* does not contain a machine-readable object (e.g., pin). In fact, row 102*b* does not contain any machine-readable object at all. In some embodiments of the present invention, a single machine-readable object may be contained within a particular row to indicate that the particular row, and any rows immediately subsequent to that row on the right which do not contain any machine-readable objects, contains objects (e.g., screws) which are described by the data on the machine-readable object in the particular row. For example, in FIG. 1, the fact that row 102*a* contains a machine-readable object 108*a* and that the immediately adjacent row 102*b* to the right of row 102*a* does not contain any machine-readable objects means that the machine-readable object 108*a* in row 102*a* contains data representing information describing any and all objects in both row 102*a* and 102*b*. More generally, the machine-readable object in a particular row may contain data representing information describing objects in that particular row and in all subsequent rows to the right up to but not including the next row that contains a machine-readable object. In the example of FIG. 1, row 102*c* contains a machine-readable object 108*b* in row 102*c*; therefore, the machine-readable object 108*a* in row 102*a* contains data representing information about objects in rows 102*a* and 102*b* but not 102*c*.

The scheme described above for using a single machine-readable object to describe objects in multiple rows is merely an example and not a limitation of the present invention. As an alternative, for example, machine-readable objects may be contained in each and every row containing objects about which information is desired.

Returning to the particular example shown in FIG. 1, row 102*c* contains: (1) machine-readable object 108*b* (e.g., pin) in slot 106*c*; and (2) screws in various slots. Machine-readable object 108*b* includes a non-transitory storage medium containing data representing information about the screws (if any) contained in the slots of row 102*c*. Note that because row 102*d* does not contain a machine-readable object, then according to the scheme described above, the data contained on the storage medium of machine-readable object 108*b* represents information describing any and all objects in both rows 102*c* and 102*d*.

Finally, in the particular example shown in FIG. 1, row 102*e* contains: (1) machine-readable object 108*c* (e.g., pin) in slot 106*e*; and (2) screws in various slots. Machine-readable object 108*c* includes a non-transitory storage medium containing data representing information about the screws (if any) contained in the slots of row 102*e*.

As described above, different rows in the tray 100 may contain objects (e.g., screws) having properties that differ from each other. For example, each row may contain objects that share the same or substantially the same properties as each other (e.g., manufacturer, model number, part number, stock keeping unit (SKU), length, and/or width), but different rows may contain objects whose properties differ from the properties of objects contained in other rows. For example, in the embodiment illustrated in FIG. 1, the objects contained in rows 102*a* and 102*b* may have the same or substantially the same properties as each other, the objects contained in rows 102*c* and 102*d* may have the same or substantially the same properties as each other, and the objects contained in row 102*e* may have the same or substantially the same properties as each other, but the properties of the objects contained in rows 102*a-b* may differ from the properties of the objects contained in rows 102*c-d* and 102*e*, the properties of the objects contained in rows 102*c-d* may differ from the properties of the objects contained in rows 102*a-b* and 102*e*, and the properties of the objects contained in row 102*e* may differ from the properties of the objects contained in rows 102*a-b* and 102*c-d*.

Because the machine-readable object in each row contains a storage medium containing data representing information about the objects in that row, the data contained on the machine-readable objects in different rows in the tray 100 may differ from each other to reflect the differences in properties of the corresponding objects. For example, assume that the objects in a particular row A of the tray 100 have a first set of properties, that the objects in another particular row B of the tray 100 have a second set of properties, and that the first and second set of properties differ from each other. As a result, the machine-readable object corresponding to (e.g., contained within the same row as) the objects in row A will contain data representing the first set of properties and the machine-readable object corresponding to (e.g., contained within the same row as) the objects in row B will contain data representing the second set of properties. Because the first and second sets of properties differ from each other, the data contained in the two machine-readable objects will also differ from each other. This may be true not only for two machine-readable objects in the tray 100, but for any number of machine-readable objects in the tray 100.

As the above description illustrates, one embodiment of the present invention is directed to a tray, or a portion thereof for containing screws and/or object objects, in which one or more machine-readable objects containing machine-readable data have been inserted into slots in the tray, such that the locations of the slots in which the machine-readable objects have been inserted correspond to properties of the objects (e.g., screws) which are in the same rows as the machine-readable objects.

Figure 3:
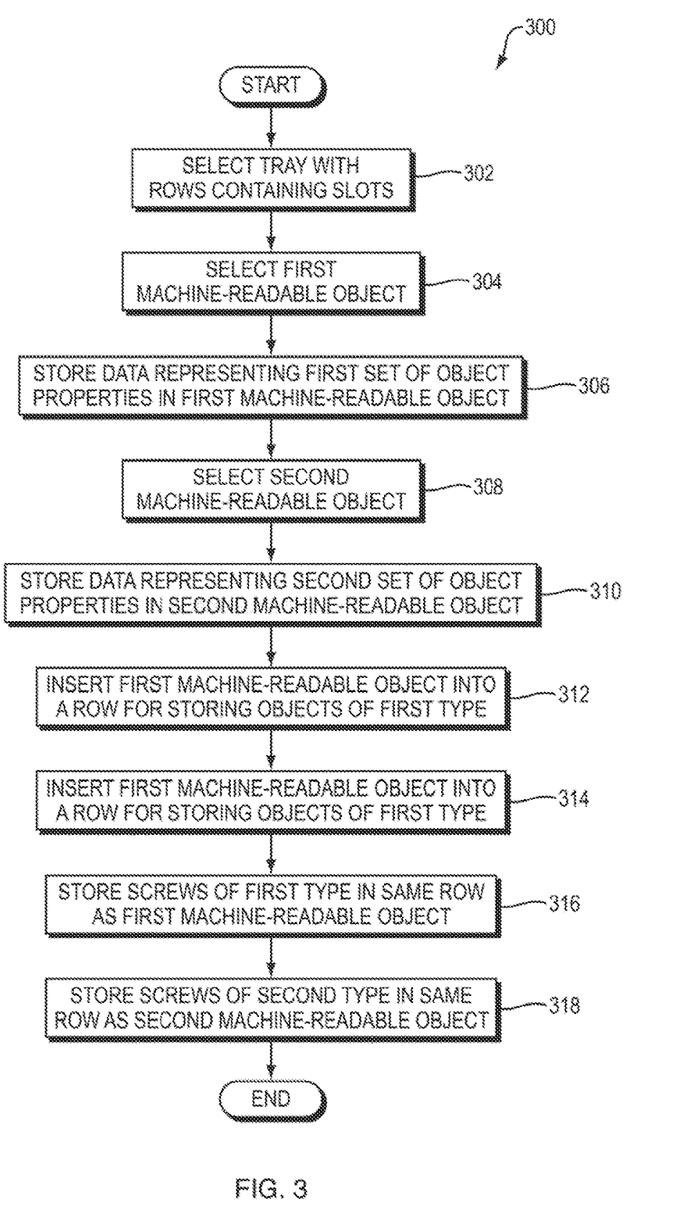
FIG. 3 is a flowchart of a method performed by one embodiment of the present invention to load a tray with objects and corresponding machine-readable objects.

Another embodiment of the present invention is directed to a method for configuring a tray of the kind described above. Referring to FIG. 3, a flowchart is shown of such a method 300 according to one embodiment of the present invention. The method 300 includes selecting a tray having a plurality of rows, where each of the plurality of rows includes a plurality of slots (FIG. 3, operation 302). A first set of object properties is identified, such as a set of properties of a first kind of object (e.g., screw). The first set of properties may include any one or more of the kinds of properties described above. A first machine-readable object is selected (e.g., a pin containing a chip) (FIG. 3, operation 304), and data representing some or all of the first set of object properties is stored in the first machine-readable object (FIG. 3, operation 306).

A second set of object properties is identified, such as a set of properties of a second kind of object (e.g., screw). The second set of properties may include any one or more of the kinds of properties described above. The second set of properties may differ from the first set of properties in whole or in part. For example, the second set of properties may include a SKU or length that differs from the SKU or length of the first set of properties. A second machine-readable object is selected (e.g., a pin containing a chip) (FIG. 3, operation 308), and data representing some or all of the second set of object properties is stored in the second machine-readable object (FIG. 3, operation 310).

Note that operations 308 and 310 effectively repeat operations 304 and 306, but for a second object and second machine-readable object. Operations 304 and 306 may be repeated for any additional number of object types and corresponding machine-readable objects.

The first machine-readable object is inserted into the tray in a slot (e.g., the topmost or next topmost slot) of a row in which objects (e.g., screws) of the type represented by the data in the first machine-readable object are stored, or will be stored (FIG. 3, operation 312). Similarly, the second machine-readable object is inserted into the tray in a slot (e.g., the topmost or next topmost slot) of a row in which objects (e.g., screws) of the type represented by the data in the second machine-readable object are stored, or will be stored (FIG. 3, operation 314). Note that operation 314 effectively repeats operation 312, but for a second machine-readable object. Operation 312 may be repeated for any additional number of machine-readable objects.

One or more objects (e.g., screws) of the type represented by the data in the first machine-readable object are inserted into the same row in the tray as the first machine-readable object (FIG. 3, operation 316). One or more objects (e.g., screws) of the type represented by the data in the second machine-readable object are inserted into the same row in the tray as the second machine-readable object (FIG. 3, operation 318). Note that operation 318 effectively repeats operation 316, but for a second machine-readable object and corresponding type of object. Operation 316 may be repeated for any additional number of machine-readable objects and corresponding types of objects.

The result of performing method 300 is to populate a tray, such as the tray shown in FIG. 1, with machine-readable objects and corresponding types of objects (e.g., screws) in the same rows as those machine-readable objects, so that the removal of such objects from the tray may be detected, such as in the manner described below in connection with FIG. 4.

The order of the steps shown in FIG. 3 is merely an example and does not constitute a limitation of the present invention. The steps of method 300 may be performed in orders other than the order shown in FIG. 3. For example, steps 316 and 318 may be performed before steps 312 and 314. As another example, steps 306, 306, 308, and 310 may be performed after steps 316 and 318.

Embodiments of the present invention include methods for reading data from machine-readable objects (such as the machine-readable objects 108*a-c* shown in FIG. 1) to track the removal of objects (e.g., screws) from a tray (e.g., tray 100). For example, referring to FIG. 4, a flowchart is shown of a method 400 for tracking the removal of objects from a tray (e.g., tray 100) according to one embodiment of the present invention.

Figure 4:
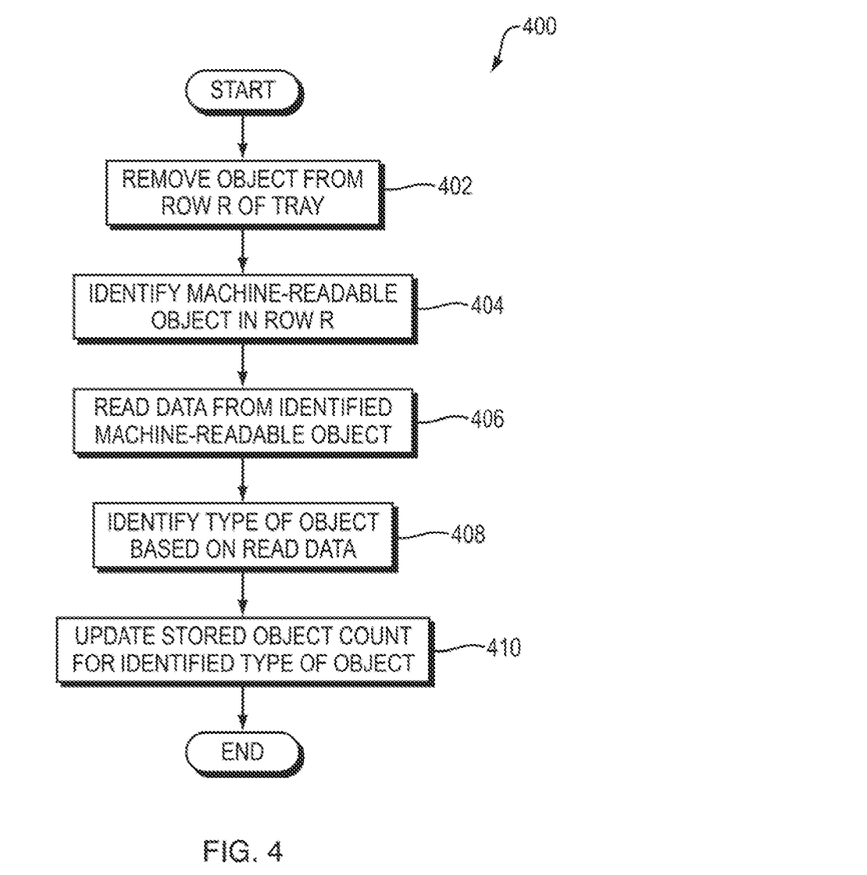
FIG. 4 is a flowchart of a method performed by one embodiment of the present invention to track the removal of objects from the tray.

An object (e.g., screw) is removed from a particular row R of the tray 100 (FIG. 4, operation 402). The machine-readable object in row R is identified (FIG. 4, operation 404). For example, if slot 110*a* were removed from row 102*a*, then machine-readable object 108*a* may be identified as the machine-readable object in the same row as slot 110*a*.

One or more units of data are read from the identified machine-readable object 108*a* (FIG. 4, operation 406). Such data may be read in any of a variety of ways. For example, a wand may be positioned (e.g., by a human operator) over the surface of the machine-readable object, thereby causing the wand to read some or all of the data from the machine-readable object. The wand or other reading device may be triggered to read data from the machine-readable object in response to input from the human operator, such as the pressing of a button.

A computer (not shown) may automatically identify the type (e.g., length) of the removed object based on the data read from the machine-readable object (FIG. 4, operation 408). For example, if the data read from the machine-readable object include data which expressly specifies a type of the removed object, then the computer may identify the type of the removed object as the type expressly specified by the read data. As another example, the computer may derive the type of the removed object from the data read from the machine-readable object. For example, if the data read from the machine-readable object specifies a length of the removed object, then the computer may derive the type of the removed object from the specified length, such as by using a table or other data structure to correlate the specified length with an object type (e.g., part number or SKU).

The method 400 decrements a stored count of the identified object type (FIG. 4, operation 410). For example, the computer may include a database or other data structure containing counts of various types of objects. As a particular example, such a data structure may begin with a count, for each of the object types initially stored in the tray 100, of the number of objects of that type initially stored in the tray. For example, in the embodiment shown in FIG. 1, if rows 102a and 102b initially contain, in aggregate, ten screws of length 3, then the data structure stored in the computer may initially contain data indicating that the tray 100 contains ten screws of length 3. In this example, in operation 410, the computer may decrement that count in response to determining that a screw was removed from row 102a or 102b.

In addition to or instead of decrementing the stored count of the identified object type, the method 400 may increment a count of the number of objects of the identified object type that have been removed from the tray 100. For example, the computer may initially contain data indicating that zero objects of each object type have been removed from the tray, such as when the method 300 of FIG. 3 is performed to initially load the tray. Then, as each object is removed from the tray 100, the method 400 may increment a count of the number of objects of that type that have been removed from the tray 100.

Operations 402-410 may be repeated for any number of objects removed from the tray 100. The function performed by the method 400 is to maintain an accurate count of the number of objects removed from the tray.

Embodiments of the present invention have a variety of advantages. For example, by enabling the removal of objects (e.g., screws) from the tray to be tracked by reading machine-readable data from machine-readable objects in the tray, and thereby automatically updating a count of such removed objects in a computer, embodiments of the present invention decrease the effort, increase the speed, and increase the accuracy of such tracking in comparison to prior art object removal tracking methods. In particular, embodiments of the present invention eliminate the need for any human operator to write down or manually enter data specifying the objects removed from the tray 100. This significantly decreases the complexity of the tracking process and enables such tracking to be performed nearly instantly after an object has been removed from the tray.

Other industries, and even departments within hospitals other than the surgical department, consider scanning at the point of use to be the gold standard for supply chain accuracy and management because of the wide range of benefits that it provides. Such scanning at the point of use, however, has not been implemented or even possible until the advent of the present invention, which uses a combination of novel and nonobvious technical means to enable screws and other supplies to be scanned at the point of use, e.g., during surgical procedures in the sterile field at the time at which such supplies are used. Embodiments of the present invention take all of the advantages of scanning at the point of use and apply them to the surgical context.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more machines, such as computers, computer processors, and/or other elements of a computer system. Such features are either impossible or impractical to implement mentally and/or manually. For example, embodiments of the present invention read data from a machine-readable object, such as by using a wand to read data from a chip. This function cannot be performed by a human manually or mentally.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method for use with an implant tray, the implant tray comprising:
   a plurality of rows of slots;
   a first machine-readable object in a first one of the plurality of rows of slots, the first machine-readable object including a first non-transitory machine-readable storage medium containing first data representing a first property of at least one first supply; and
   a first supply in the first one of the plurality of rows of slots, wherein the first supply has the first property,
   the method comprising:
   (1) reading the first data from the first non-transitory machine-readable storage medium;
   (2) identifying a type of the first supply based on the first data read from the first non-transitory machine-readable storage medium; and
   (3) updating a stored count of the type of the first supply.

2. The method of claim 1, wherein the first machine-readable object comprises a peg.

3. The method of claim 1, wherein the first supply comprises a screw.

4. The method of claim 1, wherein (3) comprises incrementing the stored count of the type of the first supply.

5. The method of claim 1, wherein (3) comprises decrementing the stored count of the type of the first supply.

6. The method of claim 1, wherein the type of the first supply comprises a length of the first supply.

7. The method of claim 1, wherein (1) comprises reading the first data using a wand.

8. The method of claim 1, further comprising removing the first supply from the tray before (1).

* * * * *